United States Patent [19]

Robson

[11] Patent Number: 5,017,606
[45] Date of Patent: May 21, 1991

[54] FLUOROBENZYL ESTERS

[75] Inventor: Michael J. Robson, Bracknell, United Kingdom

[73] Assignee: Imperial Chemical Industries PLC, London, England

[21] Appl. No.: 536,078

[22] Filed: Jun. 11, 1990

Related U.S. Application Data

[63] Continuation of Ser. No. 133,665, Dec. 14, 1987, abandoned.

[30] Foreign Application Priority Data

Dec. 12, 1986 [GB] United Kingdom ............... 8629806

[51] Int. Cl.$^5$ ............................................. A01N 53/00
[52] U.S. Cl. ................................. 514/531; 514/544; 560/105; 560/124
[58] Field of Search ............... 560/124, 105; 514/531, 514/544

[56] References Cited

U.S. PATENT DOCUMENTS

| | | | |
|---|---|---|---|
| 3,509,180 | 4/1970 | Elliott | 260/347.4 |
| 4,370,346 | 1/1983 | Punja | 424/305 |
| 4,405,640 | 9/1983 | Punja | 424/305 |
| 4,486,355 | 12/1984 | Bentley et al. | 260/465 G |
| 4,515,808 | 5/1985 | Elliott | 560/124 |
| 4,551,546 | 11/1985 | Punja | 560/124 |
| 4,594,355 | 6/1986 | Elliott | 560/124 |
| 4,611,010 | 9/1986 | Schwarz | 560/174 |
| 4,668,701 | 5/1987 | Elliott | 560/124 |
| 4,668,702 | 5/1987 | Elliott | 560/124 |
| 4,762,835 | 8/1988 | Whittle | 514/256 |

FOREIGN PATENT DOCUMENTS 0060617  9/1982  European Pat. Off. .
0196156 10/1986  European Pat. Off. .

Primary Examiner—Michael L. Shippen
Attorney, Agent, or Firm—Cushman, Darby & Cushman

[57] ABSTRACT

Fluorobenzyl esters of the formula:

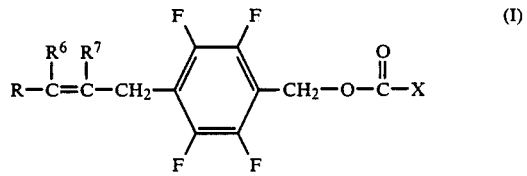

(I)

wherein X represents the residue of any carboxylic acid of formula X-COOH which forms an insecticidally active ester with a 3-phenoxybenzyl alcohol, and R, $R^6$ and $R^7$ are each selected from hydrogen, halogen and alkyl of up to four carbon atoms, provided that at least one of R, $R^6$ and $R^7$ represents halogen, and further provided that R and $R^6$ are not both bromine when $R^7$ is hydrogen. The compounds are useful for combatting insect and acarine pests.

5 Claims, No Drawings

FLUOROBENZYL ESTERS

This is a continuation of application Ser. No. 07/133,665, filed on Dec. 14, 1987, which was abandoned upon the filing hereof.

This invention relates to novel fluorobenzyl esters useful as insecticides and acaricides, to insecticidal and acaricidal compositions comprising them, to processes and intermediates for their preparation and to methods of combating insect, acarine and similar invertebrate pests using them.

The novel fluorobenzyl esters of this invention have the general formula:

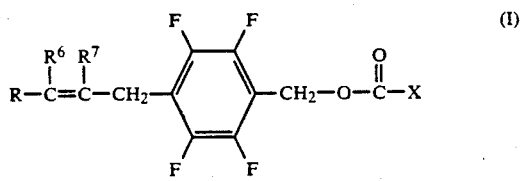

wherein X represents the residue of any carboxylic acid of formula X—COOH which forms an insecticidally active ester with a 3-phenoxybenzyl alcohol, and R, $R^6$ and $R^7$ are each selected from hydrogen, halogen and alkyl of up to four carbon atoms, provided that at least one of R, $R^6$ and $R^7$ represents halogen, and further provided that R and $R^6$ are not both bromine when $R^7$ is hydrogen. More particularly X represents either:

(a) a group of formula:

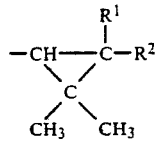

wherein (i) $R^1$ and $R^2$ are each selected from hydrogen, halo and alkyl of up to four carbon atoms, or (ii) $R^1$ is hydrogen and $R^2$ represents either a group of formula:

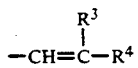

or a group of formula:

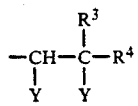

where $R^3$ and $R^4$ are each selected from methyl, halo, or haloalkyl of one or two carbon atoms containing at least two fluorine atoms, and Y is chloro or bromo; or (b) X represents a group of formula:

where $R^5$ represents an alkyl group of up to four carbon atoms and Ar represents a phenyl group optionally substituted with one or two halogen atoms.

Preferred compounds according to the invention are those of formula IA:

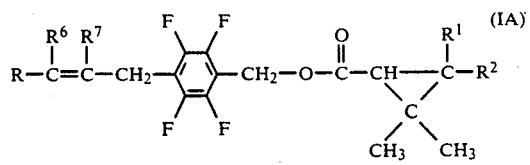

wherein R, $R^6$ and $R^7$ have any of the meanings given hereinabove, and $R^1$ and $R^2$ are each selected from halogen and alkyl of up to four carbon atoms (preferably methyl), or $R^1$ is hydrogen and $R^2$ is a group of formula:

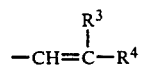

wherein $R^3$ and $R^4$ are each selected from methyl, fluoro, chloro, bromo and trifluoromethyl.

Particularly preferred compounds according to formula IA are those set out in Table I below wherein the meaning of R, $R^1$, $R^2$, $R^6$ and $R^7$ are set out for each compound.

TABLE I

| COMPOUND | R | $R^6$ | $R^7$ | $R^1$ | $R^2$ |
|---|---|---|---|---|---|
| 1 | H | Cl | H | $CH_3$ | $CH_3$ |
| 2 | H | Cl | H | H | $-CH = C(CH_3)_2$ |
| 3 | H | Cl | H | H | $-CH = CCl_2$ |
| 4 | H | Cl | H | H | $-CH = CBr_2$ |
| 5 | H | Cl | H | H | $-CH = CF_2$ |
| 6 | H | Cl | H | H | $-CH = C(F)CF_3$ |
| 7 | H | Cl | H | H | $-CH = C(Cl)CF_3$ |
| 8 | H | Cl | H | H | $-CH = C(Br)CF_3$ |
| 9 | H | Cl | H | H | $-CH = C(CF_3)_2$ |
| 10 | H | Cl | H | Cl | Cl |
| 11 | H | H | F | H | $-CH = C(Cl)CF_3$ |
| 12 | Br | H | Br | H | $-CH(Br)-C(Br)Cl_2$ |
| 13 | Br | H | Br | H | $-CH = C(Cl)CF_3$ |
| 14 | Cl | Cl | H | H | $-CH = C(Cl)CF_3$ |
| 15 | H | H | Cl | H | $-CH = C(Cl)CF_3$ |
| 16 | H | H | Br | H | $-CH = C(Cl)CF_3$ |
| 17 | Br | H | H | H | $-CH = C(Cl)CF_3$ |
| 18 | Cl | H | $CH_3$ | H | $-CH = C(Cl)CF_3$ |
| 19 | Cl | H | Cl | H | $-CH = C(Cl)CF_3$ |
| 20 | Cl | H | Cl | H | $-CH = C(F)CF_3$ |
| 21 | Cl | H | Cl | H | $-CH = CCl_2$ |
| 22 | Cl | H | Cl | $CH_3$ | $CH_3$ |

It will be appreciated that certain of the compounds of the invention wherein $R^1$ and $R^2$ are not identical are capable of existing in more than one isomeric form, due to the possibility of cis and trans isomerism in the substitution pattern of the cyclopropane ring and the presence of chiral centres at $C_1$ and $C_3$ of the cyclopropane ring. Thus there may be (+)-cis, (−)-cis, (+)-trans and (−)-trans isomers. Where $R^2$ represents a group of formula $-CH=C(R^3)R^4$ and $R^3$ and $R^4$ are not identical, there exists the further possibility of E and Z isomers of the group $R^2$. In addition, there is the still further possibility of E and Z isomers in the alcohol moiety of the invention compounds according to certain combinations of the values of R, $R^6$ and $R^7$. The scope of the invention includes each of the said isomeric forms in isolation as well as mixtures thereof, including racemic mixtures.

Examples of the preferred compounds according to formula IA include 4-(2-chloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product I)

4-(2-bromoprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product II)

4-(2-fluoroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product III)

4-(EZ-3-chloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (E:Z ratio of alcohol moiety 2:1, Product IV; E:Z ratio of alcohol moiety 1:9, Product VI)

4-(E-3-chloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product V)

4-(EZ-3-bromoprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (E:Z ratio of alcohol moiety 3:1, Product VII) 4-(EZ-3-chloro-2-methylprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (E:Z ratio of alcohol moiety 1:4, Product VIII)

4-(3,3-dichloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product IX)

4-(E-2,3-dichloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product X)

4-(E-2,3-dibromoprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product XI)

4-(E-2,3-Dibromoprop-2-en-1-yl)-2,3,5,6-tetrafluorobenzyl (±)-cis-3-[(RS)-1,2-dibromo-2,2-dichloroethyl]-2,2-dimethylcyclopropanecarboxylate (Product XII)

4-(E-2,3-dichloroprop-2-en-1-yl)-2,3,5,6-tetrafluorobenzyl (±)-trans-3-(Z-2-chloro-3,3,3-trifluoroprop-1-en-1-yl)-2,2-dimethylcyclopropanecarboxylate (Product XIII)

4-(E-2,3-dichloroprop-2-en-1-yl)-2,3,5,6-tetrafluorobenzyl (±)-cis-3-(2,2-dichloroethenyl)-2,2-dimethylcyclopropanecarboxylate (Product XIV)

4-(E-2,3-dichloroprop-2-en-1-yl)-2,3,5,6-tetrafluorobenzyl (±)-trans-3-(2,2-dichloroethenyl)-2,2-dimethylcyclopropanecarboxylate (Product XV)

4-(E-2,3-dichloroprop-2-en-1-yl)-2,3,5,6-tetrafluorobenzyl 2,2,3,3-tetramethylcyclopropanecarboxylate (Product XVI)

4-(EZ-3-chloroprop-2-en-1-yl)-2,3,5,6-tetrafluorobenzyl (±)-cis-3-(2,2-dichloroethenyl)-2,2-dimethylcyclopropanecarboxylate 4-(EZ-3-chloroprop-2-en-1-yl)-2,3,5,6-tetrafluorobenzyl (±)-trans-3-(2,2-dichloroethenyl)-2,2-dimethylcyclopropanecarboxylate 4-(E-2,3-dichloroprop-2-en-1-yl)-2,3,5,6-tetrafluorobenzyl (±)-cis-3-(Z-2,3,3,3-tetrafluoroprop-1-en-1-yl)-2,2-dimethylcyclopropanecarboxylate 4-(E-2,3-dichloroprop-2-en-1-yl)-2,3,5,6-tetrafluorobenzyl (±)-trans-3-(Z-2,3,3,3-tetrafluoroprop-1-en-1-yl)-2,2-dimethylcyclopropanecarboxylate 4-(EZ-3-chloroprop-2-en-1-yl)-2,3,5,6-tetrafluorobenzyl (±)-cis-3-(Z-2,3,3,3-tetrafluoroprop-1-en-1-yl)-2,2-dimethylcyclopropanecarboxylate 4-(EZ-3-chloroprop-2-en-1-yl)-2,3,5,6-tetrafluorobenzyl (±)-trans-3-(Z-2,3,3,3-tetrafluoroprop-1-en-1-yl)-2,2-dimethylcyclopropanecarboxylate The compounds of the invention are esters and may be prepared by conventional esterification processes, of which the following are examples.

(a) An acid of formula (II)

where X has any of the meanings given hereinabove, may be reacted directly with a 4-haloalkenyl-2,3,5,6-tetrafluorobenzyl alcohol of formula (III):

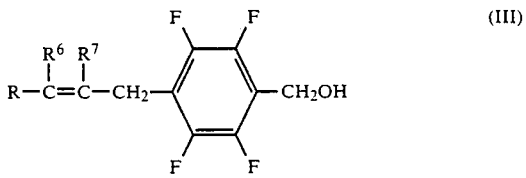

where R, $R^6$ and $R^7$ have any of the meanings given hereinabove, the reaction preferably taking place in the presence of an acid catalyst, for example, dry hydrogen chloride, or a dehydrating agent, for example, a carbodiimide such as N,N'-dicyclohexylcarbodiimide.

(b) An acid halide of formula X—COHal where Hal represents a halogen atom, preferably a chlorine atom, and X has any of the meanings given hereinabove, may be reacted with the alcohol of formula (III), the reaction preferably taking place in the presence of a base, for example, pyridine, a trialkylamine, or an alkali metal hydroxide or carbonate.

(c) An acid of formula (II) where X has any of the meanings given hereinabove, or preferably, an alkali metal salt thereof, may be reacted with a halide of formula (IV):

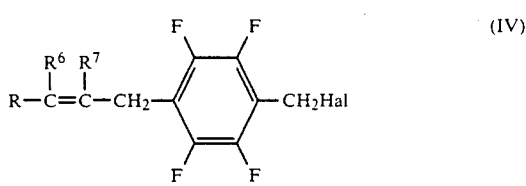

where Hal represents a halogen atom, preferably the bromine or chlorine atom, and R, $R^6$ and $R^7$ have any of the meanings given hereinabove, or with the quaternary ammonium salts derived from such halides by reaction with tertiary amines, for example pyridine, or a trialkylamine such as triethylamine.

(d) A lower alkyl ester of formula X—COOQ where Q represents a lower alkyl group containing up to six carbon atoms, preferably the methyl or ethyl group, and X has any of the meanings given hereinabove, is heated with the alcohol of formula (III) to effect a transesterification reaction. Preferably the process is performed in the presence of a suitable catalyst, for example, an alkali metal alkoxide, such as sodium methoxide, or an alkylated titanium derivative, such as tetramethyl titanate or tetraethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of the compounds described in (a) to (d) above. These may be obtained by conventional isomer separation techniques from mixtures of isomers. Thus, for example, cis and trans isomers of the compounds of formula (II) may be separated by fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the alcohol of formula (III) to produce a compound of formula (I) in the form of an individually pure isomer thereof.

4-Haloalkenyl-2,3,5,6-tetrafluorobenzyl alcohols (III) have not been described previously. In a further aspect therefore the invention provides 4-haloalkenyl-2,3,5,6-tetrafluorobenzyl alcohols of formula (III), wherein R, $R^6$ and $R^7$ have any of the meanings given above, as novel intermediates useful in the preparation of the insecticidal esters of the invention. Specific examples of the alcohols of formula (III) according to this invention include those for which values of R, $R^6$ and $R^7$ are listed in Table II, and stereoisomers thereof, where geometric isomerism is possible.

TABLE II

| Compound | R  | $R^6$ | $R^7$ |
|----------|----|----|----|
| A        | H  | H  | Cl |
| B        | H  | H  | Br |
| C        | H  | H  | F  |
| D        | H  | Cl | H  |
| E        | Br | H  | H  |
| F        | Cl | H  | CH$_3$ |
| G        | Cl | Cl | H  |
| H        | Br | H  | Br |
| J        | Cl | H  | Cl |

These compounds may be prepared from a derivative of a 4-halo-2,3,5,6-tetrafluorobenzylalcohol in which the hydroxy function has been reversibly protected, and an appropriately substituted halopropene of formula (V):

where R, $R^6$ and $R^7$ have any of the meanings described hereinabove and X represents a halogen of at least the same, and preferably greater atomic weight than the halogen of highest atomic weight represented by R, $R^6$ or $R^7$, in the presence of an alkyllithium, preferably n-butyllithium, and a cuprous halide catalyst, followed by deprotection of the hydroxy function; this method is illustrated, by way of example only, in Scheme I.

Scheme I

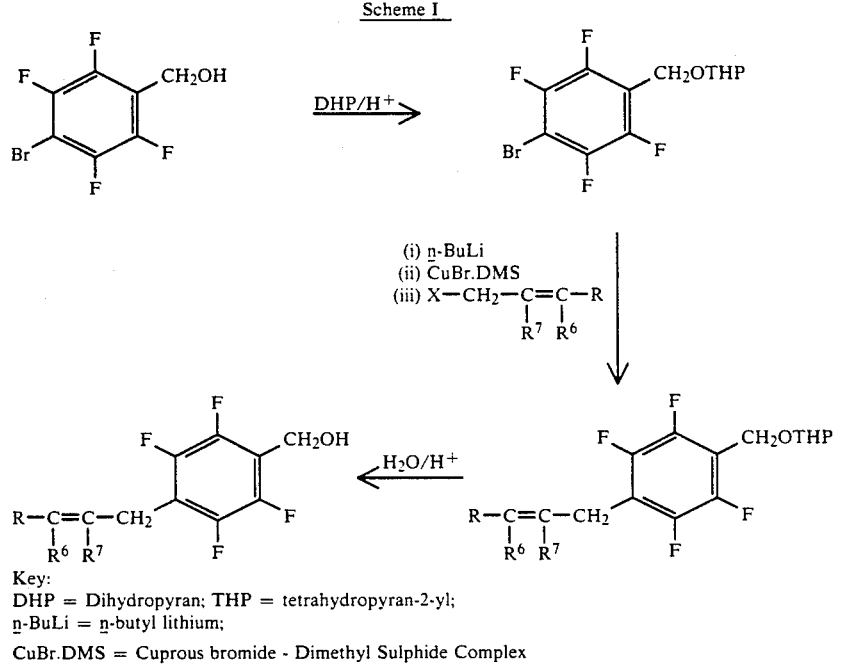

Key:
DHP = Dihydropyran; THP = tetrahydropyran-2-yl;
n-BuLi = n-butyl lithium;
CuBr.DMS = Cuprous bromide - Dimethyl Sulphide Complex Where R is hydrogen or alkyl of up to four carbon atoms and either both of $R^6$ and $R^7$ are chlorine or both of $R^6$ and $R^7$ are bromine, the alcohols of formula (III) may alternatively be prepared by the addition reaction between a derivative of a compound of formula (VI):

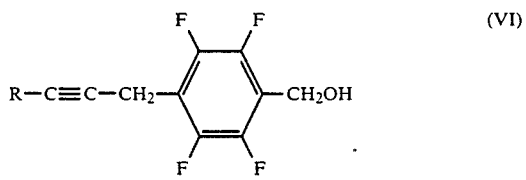

wherein R represents hydrogen or alkyl of up to four carbon atoms, in which the hydroxy function has been reversibly protected, and an equimolar quantity of a halogen selected from chlorine and bromine. Halogen addition may alternatively be achieved by reaction between the compound of formula (VI) and a cupric halide-lithium halide mixture selected from cupric chloride-lithium chloride and cupric-bromide-lithium bromide. These methods are illustrated, by way of example only, in Scheme II.

Scheme II

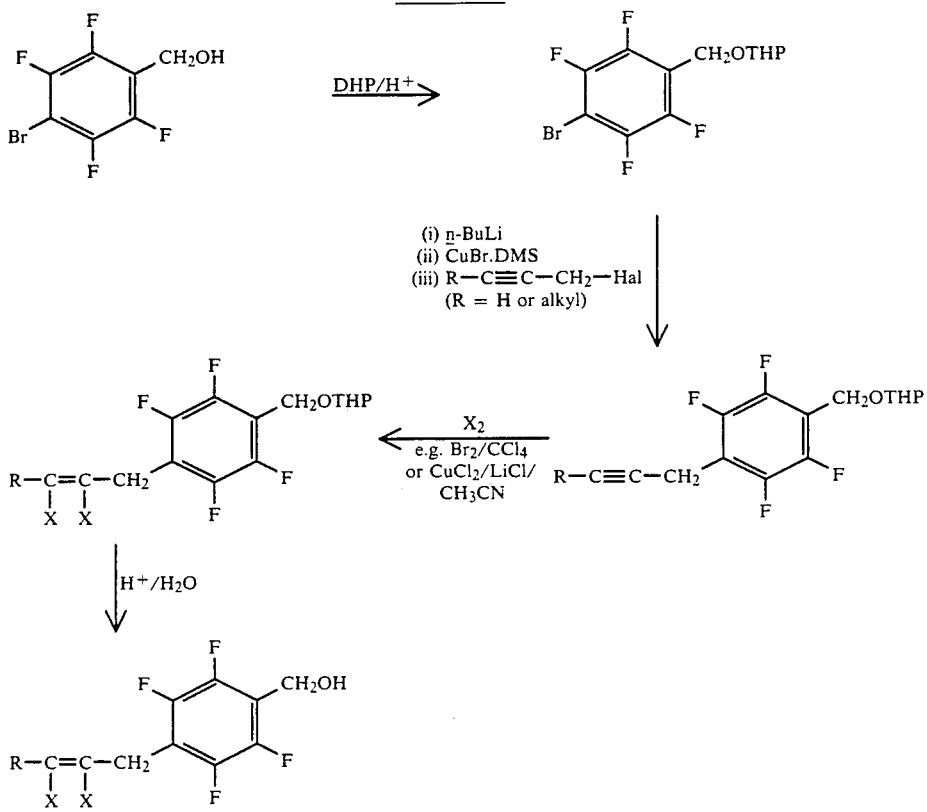

X = Cl or Br, R = H or alkyl
Key:
DHP = Dihydropyran
THP = Tetrahydropyran-2-yl
n-BuLi = n-Butyl lithium
CuBr.DMS = Cuprous bromide - Dimethyl Sulphide Complex Further details concerning the preparation and characterisation of the compounds of the invention are given hereinafter in the Examples.

The compounds of formula (I) may be used to combat and control infestations of insect and acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergist, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrins, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenofos, sulprofos, dichlorvos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion and diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones and synthetic mimics thereof such as juvenile hormone, juvabione, ecdysones, methoprene and hydroprene.

(h) Pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips, sprays or aerosols. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes. In a preferred form, aerosol compositions may contain from 0.005% to 4% of active ingredient or ingredients, the remainder of the composition comprising a solvent, selected from odourless kerosine and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and optionally adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 1–99% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of formula (I) and compositions comprising them are very toxic to wide varieties of insect, acarine and other invertebrate pests, including, for example, the following:

*Myzus persicae* (aphids)
*Aphis fabae* (aphids)
*Megoura viceae* (aphids)
*Aedes aegypti* (mosquitos)
*Anopheles spp.* (mosquitos)
*Culex spp.* (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Aonidiella spp.* (scale insects)
*Trialeuroides spp.* (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
*Diabrotica spp.* (rootworms)
*Agrotis spp.* (cutworms)
*Chilo partellus* (maize stem borers)
*Nilaparvata lugens* (plant hoppers)
*Nephotettix cincticeps* (leaf hoppers)
*Panonychus ulmi*
*Panonychus citri*
*Tetranychus urticae* (red spider mite)
*Tetranychus cinnabarinus* (carmine spider mite)

The compounds according to formula (I) and compositions comprising them have been shown to be particularly useful in controlling lepidopteran pests of cotton, for example *Spodoptera spp.* and *Heliothis spp.*, acarine pests such as *Tetranychus spp.* and *Panonychus spp.*, and public health pests such as flies and mosquitos. They have also been shown to be particularly useful in combating pests which inhabit the soil, for example *Diabrotica spp.* by virtue of their fumigant activity. They may also be useful in combating insect and acarine pests which infest domestic animals, such as *Lucilia sericata* and ixodid ticks such as *Boophilus spp., Ixodes spp., Amblyomma spp., Rhipicephalus spp.*, and *Dermaceutor spp.* They are effective in combating both susceptible and resistant strains of these pests in their adult, larval and intermediate stages of growth, and may be applied to the infested host animal by topical, oral or parental administration.

The following Examples illustrate various aspects of this invention. In the preparation Examples the products were usually identified and characterised by means of nuclear magnetic reasonance (NMR) spectroscopy and infra red (IR) spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chrompak CPSil 5CB column of 12.5M length and 0.2 mm internal diameter. Unless otherwise stated, the injection temperature was 100° C., and a temperature gradient of 15° C./minute employed, up to a maximum temperature of 250° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 100 MHz on a Jeol FX 100 NMR spectrometer, unless otherwise indicated. 90 MHz, 60 MHz, 270 MHz and 400 MHz $^1$H NMR spectrometry were performed using Jeol FX 90Q, Jeol PMX 60SI, Jeol FX270 and Jeol GX400 spectrometers respectively.

$^{19}$F NMR spectrometry was performed on a Jeol FX90Q spectrometer at a frequency of 84.26 MHz. All NMR shift ($\gamma$) values are quoted in ppm relative to a standard (TMS or CFCl$_3$).

Molecular Ion (M$^+$) peaks were determined on one of three mass spectrometers: Jeol DX303, Kratos MS80 or Hewlett Packard HP 5992.

The following Examples illustrates various aspects of the invention.

EXAMPLE 1

This Example illustrates the preparation of 4-bromo-2,3,5,6-tetrafluorobenzaldehyde.

A stirred mixture of pentafluorobenzaldehyde (17.7 g), anhydrous lithium bromide (8.9 g) and N-methylpyrrolidone (50 cm$^3$) was heated at 160° C. under a nitrogen atmosphere for 2 hours, after which it was cooled and poured into water. The solid precipitate was collected by filtration, washed on the filter with water and dried in a dessicator over phosphorus pentoxide. After trituration with diethyl ether the residual solid was collected to yield 4-bromopentafluorobenzaldehyde (8.4 g), mp. 105°–108° C.

Infra red (paraffin mull): 1700 cm$^{-1}$

EXAMPLE 2

This Example illustrates the preparation of 4-bromo-2,3,5,6-tetrafluorobenzyl alcohol.

Sodium borohydride (1.0 g) was added portionwise over a period of 30 minutes to a stirred solution of 4-bromo-2,3,5,6-tetrafluorobenzaldehyde (8.2 g) in methanol (80 cm$^3$) whilst the temperature was maintained within the range from −5° C. to +5° C., after which the mixture was stirred for 2 hours at the ambient temperature (ca 18° C.). The mixture was poured into water and the precipitated white solid collected by fitration, washed with water and air dried to yield 4-bromo-2,3,5,6-tetrafluorobenzyl alcohol (7.5 g), mp. 60°–62° C.

Infra red (paraffin mull): 3400(b), 1500 (b) cm$^{-1}$

EXAMPLE 3

This Example illustrates the preparation of 2-(4-bromo-2,3,5,6-tetrafluorobenzyloxy)tetrahydropyran.

Dihydropyran (3.0 g) and concentrated hydrochloric acid (0.3 cm$^3$) were added successively to a stirred solution of 4-bromo-2,3,5,6-tetrafluorobenzyl alcohol (8.4 g) in dry diethyl ether (50 cm$^3$) and the mixture stirred for a further 15 hours after which the more volatile components were removed by evaporation under reduced pressure. The residual oil was confirmed by spectroscopic analysis as being 2-(4-bromo-2,3,5,6-tetrafluorobenzyloxy)tetrahydropyran (9.5 g) of ca 95% purity.

$^1$H NMR (CDCl$_3$): 4.6 (m,3H); 3.9 (m,2H); 1.6 (m,6H)

EXAMPLE 4

This Example illustrates the stages in the preparation of 4-(2-chloroprop-2-en-1-yl)-2,3,5,6-tetrafluorobenzyl alcohol (Compound A)

(i) Preparation of 2-[4-(2-chloroprop-2-en-1-yl)-2,3,5,6-tetrafluorobenzyloxy]tetrahydropyran.

n-Butyllithium (2.5 M in hexane, 2.3 cm³) was added portionwise to a solution of 2-[4-bromo-2,3,5,6-tetrafluorobenzyloxy]tetrahydrofuran (1.7 g) in dry tetrahydrofuran (10 cm³) under an atmosphere of dry nitrogen, whilst the reaction temperature was maintained between −30° C. and −20° C. After 15 minutes, copper (I) bromide-dimethyl sulphide complex (1.2 g) was added in one portion and the reaction temperature was maintained at −10° C. for 1 hour, after which time 1,2-dichloroprop-2-ene (1 cm³) was added, the reaction temperature then being allowed to warm to +15° C. After 3 hours, water followed by saturated aqueous ammonium chloride solution was added to the reaction mixture, which was then extracted into diethyl ether. The organic layer was then washed with water and brine, dried, and the solvent evaporated under reduced pressure. The residue was then subjected to medium pressure column chromatography on a silica gel column using a Gilson apparatus, eluting with petroleum ether (boiling range 30°-40° C.) containing diethyl ether (10% by volume) to give 2-[4-(2-chloroprop-2-en-1-yl)-2,3,5,6-tetrafluorobenzyloxy]tetrahydropyran (1.5 g).

90 MHz ¹HNMR (CDCl₃): 1.4–1.9 (m,6H); 3.4–4.0 (m,4H); 4.45–4.95 (m,3H); 5.25 (d,2H)

Infra red (liquid film): 2950, 1630, 1470, 1260, and 1050 cm⁻¹

(ii) Preparation of 4-(2-chloroprop-2-en-1-yl)-2,3,5,6-tetrafluorobenzyl alcohol.

The tetrahydropyranyl ether prepared in stage (i) (0.2 g), was dissolved in methanol (6 cm³), and to the stirred solution was added concentrated hydrochloric acid (several drops). After stirring for 6 hours, and standing for a further 14 hours, the reaction mixture was poured into water, and extracted into ethyl acetate. The organic layer was washed with water and brine, dried, and the solvent evaporated under reduced pressure to give 4-(2-chloroprop-2-en-1-yl)-2,3,5,6-tetrafluorobenzyl alcohol as an orange oil (0.15 g).

90 MHz ¹H NMR (CDCl₃): 1.95 (t,1H); 3.75 (s,2H); 4.8 (d,2H); 5.25 (d,2H)

EXAMPLE 5

The following compounds were prepared from 2-(4-bromo-2,3,5,6-tetrafluorobenzyloxy)tetrahydropyran and the appropriate halopropene by a two stage procedure similar to that described in Example 4.

(i) 4-(2-Bromoprop-2-en-1-yl)-2,3,5,6-tetrafluorobenzyl alcohol, from 1,2-dibromoprop-2-ene (Compound B)

90 MHz ¹HNMR (CDCl₃): 5.6 (d, 2H); 4.85 (d, 2H); 3.9 (s, 2H); 2.02 (t, 1H).

Infra red (liquid film): 3300, 1630 cm⁻¹.

(iii) 3-(2-Fluoroprop-2-en-1-yl)-2,3,5,6-tetrafluorobenzyl alcohol (Compound C), from 1-iodo-2-fluoroprop-2-ene.

¹H NMR (CDCl₃): 4.8 (s, 2H); 4.7, 4.55 (2d, 2H); 3.64 (d, 2H); 2.25–2.0 (bs,1H)

(iii) EZ-4-(3-chloroprop-2-en-1-yl)-2,3,5,6-tetrafluorobenzyl alcohol (Compound D, E:Z ratio 2:1), from EZ-1,3-dichloroprop-2-ene (E:Z ratio 2:1).

Infra red (liquid film): 3640, 1475, 1280, 1265, 920 cm⁻¹.

(iv) E-4-(3-chloroprop-2-en-1-yl)-2,3,5,6-tetrafluorobenzyl alcohol (Compound D, E isomer), from E-1,3-dichloroprop-2-ene.

(v) EZ-4-(3-chloroprop-2-en-1-yl)-2,3,5,6-tetrafluorobenzyl alcohol (Compound D, E:Z ratio 1:9), from EZ-1-iodo-3-chloroprop-2-ene (E:Z ratio 1:9).

¹HNMR (CDCl₃): 6.2 (d, 1H); 5.85 (q, 1H); 4.8 (s, 2H); 3.7 (d, 2H); 1.95 (bs,1H)

(vi) EZ-4-(3-bromoprop-2-en-1-yl)-2,3,5,6-tetrafluorobenzyl alcohol (Compound E, E:Z ratio 3:1), from EZ-1,3-di-bromoprop-2-ene (E:Z ratio 3:1).

¹H NMR (CDCl₃): 6.65, 6.2, 5,5 (3t,2H); 4.7 (s,2H); 3.4 (bs,2H)

Infra red (liquid film): 3300, 1630 cm⁻¹.

(vii) EZ-4-(3—Chloro-2-methylprop-2-en-1-yl)-2,3,5,6-tetrafluorobenzyl alcohol (Compound F, E:Z ratio 1:4), from EZ-1-bromo-2-methyl-3-chloroprop-2-ene (E:Z ratio 1:4).

¹H NMR (CDCl₃): 5.9 (s,1H); 4.76 (s,2H); *3.68, 3.46 (2d,2H); 2 92 (s,1H); 1.8 (s,3H); *1.64 (s,3H)

\* Ratio of signals 83:17

Infra red (liquid film): 3300, 1630 cm⁻¹.

(viii) 4-(3,3-Dichloroprop-2-en-1-yl)-2,3,5,6-tetrafluorobenzyl alcohol (Compound G), from 1-bromo-3,3-dichloroprop-2-ene.

¹H NMR (CDCl₃): 5.95 (t, 1H); 4.8 (s, 2H); 3.60 (d, 2H); 2.2 (s,1H)

Infra red (liquid film): 3300, 1630 cm⁻¹.

EXAMPLE 6

4-(Prop-2-yn-1-yl)-2,3,5,6-tetrafluorobenzyl alcohol was prepared from 2-[4-bromo-2,3,5,6-tetrafluorobenzyloxy)-tetrahydropyran and propargyl chloride, by a two stage procedure similar to that described in Example 4.

¹H NMR (CDCl₃): 4.8 (s, 2H); 3.6 (m, 2H); 2.3 (broad s, 1H); 1.0 (t, 1H).

Infra red (liquid film): 3400 cm⁻¹.

EXAMPLE 7

This Example illustrates the preparation of E-4-(2,3-dibromoprop-2-en-1-yl)-2,3,5,6-tetrafluorobenzyl alcohol (Compound H, E isomer).

A solution of bromine (0.22 g) in carbon tetrachloride (10 cm³) was added dropwise to a stirred solution of 4-(prop-2-yn-1-yl)-2,3,5,6-tetrafluorobenzyl alcohol (0.3 g) in carbon tetrachloride (10 cm³) at the ambient temperatue (ca. 22° C.). The solution decolourised after a short time, and analysis by gas liquid chromatography showed completion of the reaction. The solvent was evaporated under reduced pressure to give a brown oil, which was purified by column chromatography on a silica gel support, eluting with dichloromethane, to give E-4-(2,3-dibromoprop-2-en-1-yl)-2,3,5,6-tetrafluorobenzyl alcohol (0.5 g).

¹H NMR (CDCl₃): 5.75-5.8 (2s,1H); 4.8 (s, 2H); 3.9, 4.1 (2s, 2H); 2.0–1.9 (bs,1H)

EXAMPLE 8

This Example illustrates the preparation of E-4-(2,3-dichloroprop-2-en-1-yl)-2,3,5,6-tetrafluorobenzyl alcohol, (Compound J, E isomer).

A mixture of 4-(prop-2-yn-1-yl)-2,3,5,6-tetrafluorobenzyl alcohol (0.1 g), copper (II) chloride (1.3 g), lithium chloride (0.62 g) and dry acetonitrile (23 cm³) was heated at the reflux temperature for 40 hours. The resulting dark solution was poured into dilute hydrochloric acid, and extracted into ethyl acetate. The organic phase was washed with more dilute hydrochloric acid, dried, and the solvent evaporated under reduced pressure to give E-4-(2,3-dichloroprop-2-en-1-yl)-2,3,5,6-tetrafluorobenzyl alcohol (0.1 g) as an orange oil.

$^1$H NMR (CDCl$_3$) (ppm): 4.0 (s, 2H); 4.84 (s,2H); and 6.35 (s, 1H).

Infra red (liquid film): 3400, 1490, 1285, 1055 and 820 cm$^{-1}$.

EXAMPLE 9

This Example describes the preparation of 4-(2-bromoprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product II).

A mixture of 4-(2-bromoprop-2-en-1-yl)-2,3,5,6-tetrafluorobenzyl alcohol (106 mmoles), triethylamine (106 mmoles) and dry diethyl ether was stirred at the ambient temperature (ca. 25° C). A solution of (±)-cis-3-(Z-2-chloro-3,3,3-trifluoroprop-1-en-1-yl)-2,2-dimethylcyclopropanecarboxylic acid chloride (106 mmoles) in dry diethyl ether was added to the reaction mixture over a period of 5 minutes; stirring was continued for a further one hour.

After removal of the solid component by filtration, the filtrate was concentrated by evaporation of the solvent under reduced pressure and the residual oil subjected to purification by flash column chromatography, on silica gel using dichloromethane as eluent, to give 4-(2-bromoprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (100 mmoles).

90 MHz $^1$HNMR (CDCl$_3$): 6.85 (d, 1H); 5.55 (d, 2H); 5.23 (s,2H); 3.9 (s,2H); 2.3–1.9 (m,2H); 1.3 (s,6H)

Infra red (liquid film): 1730, 1650, 1630 cm$^{-1}$.

EXAMPLE 10

This Example illustrates the preparation of 4-(2-fluoroprop-2-en-1-yl)-2,3,5,6-tetrafluorobenzyl (±)-cis3-(Z-2-chloro-3,3,3-trifluoroprop-1-en-1-yl)-2,2-dimethylcyclopropanecarboxylate (Product III).

A mixture of (±)-cis-3-(Z-2-chloro-3,3,3-trifluoroprop-1-en-1-yl)-2,2-dimethylcyclopropanecarboxylic acid (106 mmoles), 4-(2-fluoroprop-2-en-1-yl)-2,3,5,6-tetrafluorobenzyl alcohol (106 mmoles) and a catalytic amount of N,N-dimethylaminopyridine was stirred at the ambient temperature (ca. 25° C.). N,N'-Dicyclohexylcarbodiimide (100 mmoles) was added to the reaction mixture and stirring was continued for a further 1 hour.

After removal of the solid component by filtration, the filtrate was concentrated by evaporation of the solvent under reduced pressure and the residual oil subjected to purification by flash column chromatography through silica gel using dichloromethane as eluent to give pure 3-(2-fluoroprop-2-en-1-yl)-2,3,5,6-tetrafluorobenzyl (±)-cis-3-(Z-2-chloro-3,3-trifluoroprop-1-en-1-yl)-2,2-dimethylcyclopropane-carboxylate (90 mmoles).

$^1$H NMR (CDCl$_3$): 6.9 (d,1H); 5.25 (q,2H); 4.65 (dd, 1H, J=16Hz); 4.4; 4.26 (dd,1H, J=48 Hz); 2.2 (t,1H); 1.95 (d,1H); 1.3 (s,6H).

$^{19}$F NMR (CDCl$_3$): −69.275; −143.59

Infra red (liquid film): 1730, 1650, 1630 cm$^{-1}$.

EXAMPLE 11

The following compounds were prepared from the appropriate starting materials by the methods of Example 9 or Example 10.

(i) 4-(2—Chloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product I).

90 MHz $^1$HNMR (CDCl$_3$) 6.90 (d, 1H); 5.3 (s,3H); 5.2 (s, 3H); 3.75 (s, 2H); 2.25–1.90 (m,2H); 1.3 (s,6H)

Infra red (liquid film): 1730, 1650, 1630 cm$^{-1}$.

(ii) 4-(EZ-3—Chloroprop-2-en-1-yl)-2,3,5,6-tetrafluorobenzyl (±)-cis-3-(Z-2-chloro-3,3,3-trifluoroprop-1-en-yl)-2,2-dimethylcyclopropanecarboxylate (E:Z ratio of alcohol moiety 2:1) (Product IV).

90 MHz $^1$HNMR (CDCl$_3$): 6.9 (d, 1H); 6.2–6.75 (m,2H); 5.2 (s,2H); 3.7, 3,45 (2d, 1H); 2.3–1.9 (m,2H); 1.3 (s,6H)

Infra red (liquid film): 1730, 1650, 1630 cm$^{-1}$.

(iii) 4-(E-3—Chloroprop-2-en-1-yl)-2,3,5,6-tetrafluoro, benzyl (±)-cis-3-(Z-2-chloro-3,3,3-trifluoroprop-1-en-1-yl)-2,2-dimethylcyclopropanecarboxylate (Product V).

$^1$H NMR (CDCl$_3$): 6.85 (d, 1H); 5.8–6.2 (m, 2H); 5.2 (s, 2H); 3.45 (d, 2H); 2.3–1.9 (m, 2H); 1.3 (s, 6H).

Infra red (liquid film): 1730, 1650, 1630 cm$^{-1}$.

(iv) 4-(EZ-3—Chloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (E:Z ratio of alcohol moiety 1:9) (Product VI).

$^1$HNMR (CDCl$_3$): 6.9 (d, 1H); 6.15 (d,1H); 5.85 (q, 1H); 5.2 (bs, 2H); 3.7, 3.45 (2d,2H); 2.3–1.9 (m,2H); 1.3 (s,6H).

Infra red (liquid film): 1730, 1650, 1630 cm$^{-1}$.

(v) 4-(EZ-3-Bromoprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (E:Z ratio of alcohol moiety 3:1) (Product VII).

$^1$H NMR (CDCl$_3$): 6.85–6.6 (m,2H); 6.2 (m,1H); 5.2 (s,2H); 4.24 (d,2H); 3.65, 3.48 (m,2H); 2.3–1.9 (m,2H); 1.3 (s,6H).

Infra red (liquid film): 1730, 1650, 1630 cm$^{-1}$.

(vi) 4-(EZ-3—Chloro-2-methylprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (E:Z ratio of alcohol moiety 1:4) (Product VIII).

$^1$HNMR (CDCl$_3$): 6.9 (d, 1H); 5.9 (s, 1H); 5.2 (s, 2H); 3.7, 3.5 (2s, 2H); 2.3–1.9 (m, 2H); 1.8, 1.68 (2s,3H); 1.3 (s,6H).

Infra red (liquid film): 1730, 1650, 1630 cm$^{-1}$.

(vii) 4-(3,3-Dichloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product IX).

$^1$HNMR (CDCl$_3$) 6.9 (d, 1H); 5.95 (t, 1H); 5.25 (s, 2H); 3.65 (d, 2H); 2.3–1.9 (m,2H); 1.3 (s,6H).

Infra red (liquid film): 1730, 1650, 1630 cm$^{-1}$.

(viii) 4-(E-2,3-Dichloroprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product X).

$^1$H NMR (CDCl$_3$): 6.95 (d, 1H); 6.35 (s, 1H); 5.25 (s, 2H); 4.05 (s, 2H); 2.3–1.9 (m,2H); 1.3 (s,6H)

Infra red (liquid film): 1730, 1650, 1630 cm$^{-1}$.

(ix) 4-(E-2,3-dibromoprop-2-en-1-yl)-2,3,5,6-tetrafluorobenzyl (±)-cis-3-(Z-2-chloro-3,3,3-trifluoroprop-1-en-1-yl)-2,2-dimethylcyclopropanecarboxylate (Product XI).

$^1$H NMR (CDCl$_3$): 6.9 (d, 1H); 5.6 (s, 1H); 5:2 (s, 2H); 4.1 (s, 2H); 2.3–1.9 (m,2H); 1.3 (s,6H).

Infra red (liquid film): 1730, 1650, 1630 cm$^{-1}$.

(x) 4-(E-2,3-Dibromoprop-2-en-1-yl)-2,3,5,6-tetrafluorobenzyl (±)-cis-3-[(RS)-1,2-dibromo-2,2-dichloroethyl]-2,2-dimethylcyclopropanecarboxylate (Product XII).

$^1$H NMR (CDCl$_3$): 6.6 (s, 1H); 5.4–5.0 (m, 2H); 4.1 (s, 2H); 1.9 (m, 2H); 1.35 (s, 3H); 1.25 (s,3H).

Infra red (liquid film): 1730, 1650, 1630 cm$^{-1}$ (xi) 4-(E-2,3-dichloroprop-2-en-1-yl)-2,3,5,6-tetrafluorobenzyl (±)-trans-3-(Z-2-chloro-3,3,3-trifluoroprop-1-en-1-yl)-2,2-dimethylcyclopropanecarboxylate (Product XIII).

400 MHz $^1$HNMR (CDCl$_3$): 1.25 (s,3H); 1.35 (s,3H); 1.8 (d,1H); 2.45 (dd,1H); 4.0 (s,2H); 5.25 (q,2H); 6.15 (d,1H); 6.35 (s,1H).

(xii) 4-(E-2,3-dichloroprop-2-en-1-yl)-2,3,5,6-tetrafluorobenzyl (±)-trans-3-(2,2-dichloroethenyl)-2,2-dimethylcyclopropanecarboxylate (Product XV).

270 MHz $^1$HNMR (CDCl$_3$): 6.32 (s,1H); 5.6 (d,1H); 5.25 (s,2H); 3.99 (s,2H); 2.28 (dd,1H); 1.6 (d,1H); 1.3 (s,3H); 1.19 (s,3H).

(xiii) 4-(E-2,3-dichloroprop-2-en-1-yl)-2,3,5,6-tetrafluorobenzyl 2,2,3,3-tetramethylcyclopropanecarboxylate (Product XVI).

270 MHz $^1$HNMR (CDCl$_3$): 6.32 (s,1H); 5.19 (s,2H); 3.99 (s,2H); 1.26 (s,6H); 1.18 (s,7H)

EXAMPLE 12

This Example illustrates the insecticidal properties of the products of this invention.

The activity of the product was determined using a variety of insect pests. The product was used in the form of liquid preparations containing 500 or 100 parts per million (ppm) by weight of the product. The preparations were made by dissolving the product in acetone and diluting the solution with water containing 0.01% by weight of a wetting agent sold under the trade name "LISSAPOL" NX until the liquid preparations contained the required concentration of the product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment. Details are given in Table III.

The results of the tests are given in Table IV for each of the products, at the rate in parts per million given in the second column as a grading of mortality designated as A, B or C wherein A indicates 80–100% mortality, B indicates 50–79% mortality and C indicates less than 50% mortality.

In Table IV the pest organism used is designated by a letter code and the pests species, the support medium or food, and the type and duration of test is give in Table III.

TABLE III

| CODE LETTERS (Table IV) | TEST SPECIES | SUPPORT MEDIUM/FOOD | TYPE OF TEST | DURATION (days) |
|---|---|---|---|---|
| TUa | Tetranychus urticae (spider mites - adult) | French bean leaf | Contact | 3 |
| TUe | Tetranychus urticae (spider mites - ova) | French bean leaf | Contact | 3 |
| MP | Myzus persicae (aphids) | Chinese Cabbage leaf | Contact | 3 |
| NL | Nilaparvata lugens (brown plant hopper - nymphs) | Rice plant | Growth | 6 |
| HV | Heliothis virescens (tobacco budworm - larvae) | Cotton leaf | Residual | 3 |
| DB | Diabrotica balteata (rootworm larvae) | Filter paper/ maize seed | Residual | 3 |
| BG | Blattella germanica (cockroach nymphs) | Plastic pot | Residual | 3 |
| MD | Musca domestica (houseflies - adults) | Cotton wool/ sugar | Contact | 1 |

TABLE IV

| COMPOUND NO. | RATE (ppm) | TUa | Tue | MP | NL | HV | DB | BG | MD |
|---|---|---|---|---|---|---|---|---|---|
| I | 500 | A | A | A | A | A | A | A | A |
| II | 500 | A | A | A | — | A | A | A | A |
| III | 100 | A | C | A | — | A | A | A | A |
| IV | 500 | A | A | A | A | A | A | A | A |
| V | 500 | A | A | C | — | A | A | C | A |
| VI | 500 | A | B | A | — | A | A | A | A |
| VII | 500 | A | A | A | A | A | A | A | C |
| VIII | 500 | A | A | A | A | A | A | A | A |
| IX | 500 | A | A | A | C | A | A | A | A |
| X | 500 | A | A | A | — | A | A | A | A |
| XI | 500 | A | A | A | C | A | A | A | A |
| XII | 500 | C | C | A | C | A | B | C | C |
| XIII | 100 | A | C | A | A* | A | A | A | C |

*Nilaparvata lugens replaced by Nephotettix cincticeps in this test.

I claim:
1. A compound of formula (I):

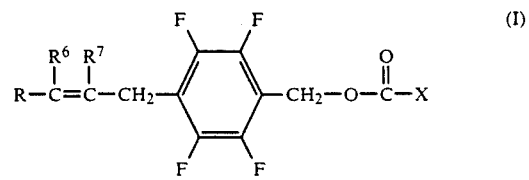

wherein X represents a group of formula:

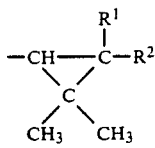

wherein (i) $R^1$ and $R^2$ are each selected from the hydrogen, halo and alkyl of up to four carbon atoms, or (ii) $R^1$ is hydrogen and $R^2$ represents either a group of formula

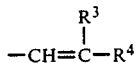

or a group of formula:

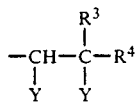

wherein $R^3$ and $R^4$ are each selected from methyl, halo or haloalkyl of one or two carbon atoms containing at least two fluorine atoms, and Y is chloro or bromo; or X represents a group of formula:

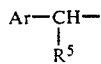

wherein $R^5$ represents an alkyl group of up to four carbon atoms and Ar represents a phenyl group optionally substituted with one or two halogen atoms, and R, $R^6$ and $R^7$ are each selected from hydrogen, halogen and alkyl of up to four carbon atoms, provided that at least one of R, $R^6$ and $R^7$ represents halogen, and further provided that R and $R^6$ are not both bromine when $R^7$ is hydrogen.

2. A compound as claimed in claim 1 having the formula (IA):

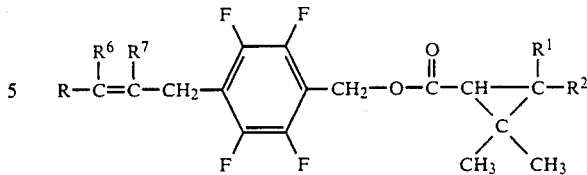

wherein R, $R^6$ and $R^7$ have any of the meanings given in claim 1, and $R^1$ and $R^2$ are each selected from halogen and alkyl of up to four carbon atoms, or $R^1$ is hydrogen and $R^2$ is a group of formula:

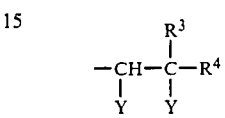

wherein $R^3$ and $R^4$ are each selected from methyl, fluoro, chloro, bromo and trifluoromethyl.

3. A compound as claimed in claim 1 wherein R, $R^6$ and $R^7$ have any of the meanings given in claim 1, and X represents the residue of an acid of formula X—COOH selected from the group of acids comprising:

(±)-cis-3-(Z-2-chloro-3,3,3-trifluoroprop-1-en-1-yl)-2,2-dimethylcyclopropanecarboxylic acid,
(±)-cis-3-[(RS)-1,2-dibromo-2,2-dichloroethyl]-2,2-dimethylcyclopropanecarboxylic acid,
(±)-trans-3-(Z-2-chloro-3,3,3-trifluoroprop-1-en-1-yl)-2,2-dimethylcyclopropanecarboxylic acid,
(±)-cis-3-(2,2-dichloroethenyl)-2,2-dimethylcyclopropanecarboxylic acid,
(±)-trans-3-(2,2-dichloroethenyl)-2,2-dimethylcyclopropanecarboxylic acid and
2,2,3,3-tetramethylcyclopropanecarboxylic acid.

4. An insecticidal and acaricidal composition comprising an insecticidally and acaricidally effective amount of a compound as defined in claim 1 in association with an insecticidally and acaricidally inert diluent or carrier.

5. A method of combating insect or acarine pests at a locus which comprises applying to the locus an insecticidally and acaricidally effective amount of a composition as defined in claim 4.

* * * * *